United States Patent [19]

Murphy

[11] 4,212,294

[45] Jul. 15, 1980

[54] ORTHOPEDIC FRACTURE FIXATION DEVICE

[76] Inventor: Frank P. Murphy, 5727 Stratford La., Lakeland, Fla. 33803

[21] Appl. No.: 20,806

[22] Filed: Mar. 15, 1979

[51] Int. Cl.³ .......................... A61B 17/18; A61F 5/04
[52] U.S. Cl. ................................................ 128/92 BC
[58] Field of Search ........... 128/92 BC, 92 B, 92 BA, 128/92 BB, 92 R, 92 G

[56] References Cited

U.S. PATENT DOCUMENTS

| 2,821,979 | 2/1958 | Cameron | 128/92 BC |
| 3,763,855 | 10/1973 | McAtee | 128/92 BC |

OTHER PUBLICATIONS

McAtee Olecranon Device, Orthopedic Catalog, Richards Mfg. Co., Memphis, Tenn., 1974 (Received 3/25/75 in Scientific Library), pp. 88-89.

Primary Examiner—Ronald L. Frinks
Attorney, Agent, or Firm—Arthur W. Fisher, III

[57] ABSTRACT

An orthopedic fixation device and method for fixation of fractures of the proximal end of the ulna comprising a first fixation member having an enlarged head and an elongated body having a threaded aperture formed in the mid-portion thereof and a threaded outer portion and a second fixation member comprising an elongated pin or a threaded flexible body having a smooth tapered tip at one end thereof and a head having a groove formed on the outer surface thereof at the opposite end thereof, specifically configured to provide a three point fixation to enhance the compression between the fractured surfaces, and to improve the rigidity and compression of fracture fixation thereby improving bone healing.

5 Claims, 4 Drawing Figures

U.S. Patent  Jul. 15, 1980  4,212,294
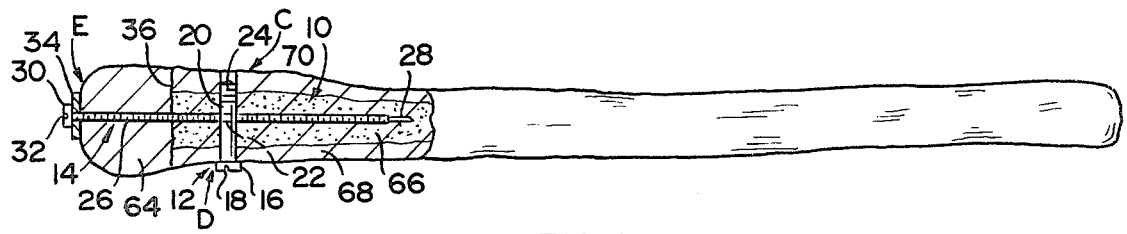
FIG. 1
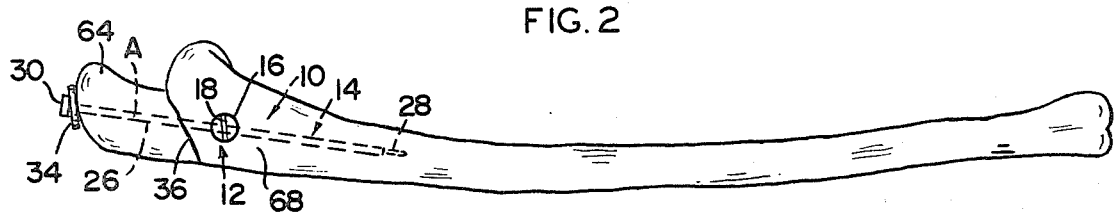
FIG. 2
FIG. 3
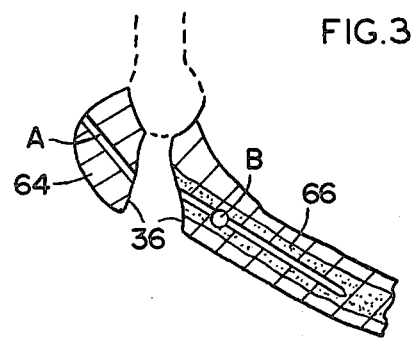
FIG. 4 (PRIOR ART)
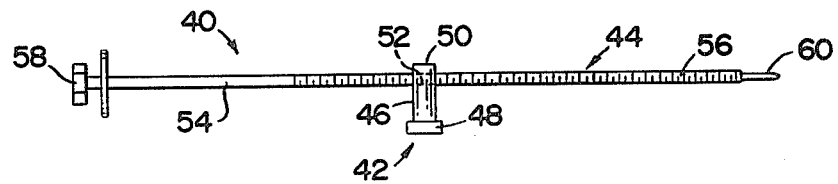

ORTHOPEDIC FRACTURE FIXATION DEVICE

BACKGROUND OF THE INVENTION

1. Field of the Invention

An orthopedic fixation device and method for fixation of fractures of the proximal end of the ulna.

2. Description of the Prior Art

To set a broken bone and maintain the bone fragments a set condition during healing, it is particularly desirable to place the bone fragments under compression to enhance the rate of healing. It is also important to secure the bone fragments of the broken bone against relative rotation with respect to each other so as to prevent inadvertent dislocation of the fragments during the healing period. Efforts have been made in the past to obtain these qualities in a bone retaining apparatus, but the prior art apparatus has been unsatisfactory, one of the main objections being that the device used maintained inadequate fixation and often broke or pulled loose. This causes non-union or mal-union. Efforts have been made to provide a bone retaining apparatus adapted to place the bone fragments in compression, to prevent rotation of the fragments during the healing period and where no part of the apparatus projects through the skin, during the healing of the bone fracture.

Also included are bone retaining apparatus disposed within the medullary cavity of a broken bone with the apparatus being anchored or secured to the bone fragments in such a manner that in certain selected types of fractures no cast will be necessary.

Particular difficulties arise with the arm including the upper arm bone, the two forearm bones, the ulna which is the bone having its lower or distal end aligned with the smallest finger of the hand, and the radius which has its distal end aligned with the thumb. The elbow joint itself includes a crescent-shaped recess in the ulna and a corresponding matching convex surface at the lower end of the humerus.

When the ulna is broken or fractured near its proximal end, at or close to the semi-lunar notch, the powerful triceps muscle tends to pull the bone fragment upward away from the main distal portion of the bone and it is difficult to set the bones in their proper relative positions for mending.

Efforts have been made to use a sort of screw which extends through a hole drilled in the end of the bone fragment and which is provided with screw threads which are directed into the soft center channel, known as the "medullary canal," of the main distal portion of the ulna. However, this procedure does not always accomodate different bone shapes and sizes and types of breaks. More specifically, it is not always possible to have the screw reach the desired tightness just as the head of the screw brings the bones into the properly set or "reduced" position, without repeated insertions and removal of the screw. The threaded end of the screw in the medullary cavity of the distal ulnar fragment often pulls out and fixation is lost.

It has also been proposed to set the ulna bone fragments, or reduce the fracture, by using metal wires or plates or absorbable material such as catgut, kangaroo tendon or the like. However, such techniques are frequently complicated by the pull of the triceps muscle, which are located on the back of the humerus, or upper arm bone. This triceps muscle normally pulls on the olecranon or upper end of the ulna to extend the forearm. When the ulna is broken near the elbow, the upper or proximal bone fragment is pulled upward, away from its normal position, by these powerful triceps muscle.

In view of the problems of reducing the fracture against the force of the triceps muscle, it has also been proposed to completely excise or remove the broken bone fragment near the elbow. However, this technique gives rise to instability of the joint and a decrease in triceps power, and has many disadvantages as can readily be appreciated.

McAtee in U.S. Pat. No. 3,763,855 endeavors to improve the art by a double incision and blindly matching of two fixation members. This has the obvious disadvantage of multiple incisions, difficulty in application and lack of firm or secure mechanical fixation to the bones themselves because of only two point of fixation.

Other prior art known to applicant are U.S. Pat. Nos. 2,381,050; 2,699,774; 2,821,979; 2,952,254; 3,118,444.

SUMMARY OF THE INVENTION

The present invention relates to an orthopedic fixation device and method for fixation of bone fractures. More specifically, the orthopedic fixation device comprises a first substantially rigid fixation member having an enlarged head and an elongated body having a threaded aperture formed on the mid-portion thereof and a threaded outer portion and a second fixation member including an elongated substantially flexible pin having a threaded flexible body and a smooth tapered tip at one end thereof and a head formed on the outer surface thereof at the opposite end thereof.

The orthopedic fixation device is used in the repair of a fractured proximal ulna near the elbow (at or near the olecranon process).

In use the arm and elbow at the fracture site are typically prepared by making a vertical incision at the posterior aspect distal arm, elbow and forearm centering over the fracture site. The fractured site is exposed and cleared of debris. A hole is then drilled through the olecranon process in line with the marrow cavity of the ulna. The marrow cavity of the distal ulna is cleared of soft tissue with a currette and its alignment determined. Through the same incision a second hole is drilled laterally of the length of the marrow canal through the surface of the ulna, through the marrow canal, and into the opposite cortex. Once the fractured arm is thus prepared the first fixation member is placed in the second drilled hole and screwed in the opposite cortex by the threaded outer portion insuring that the threaded aperture is properly oriented to the proximal end of the ulna to permit alignment thereof with the threaded flexible body. Since the first fixation member includes a threaded outer portion, the first fixation member may be securely attached immediately adjacent the fracture permitting the single incision method to accommodate visual alignment. The threaded flexible body is then passed through the first drilled hole (one washer is usually used) such that the smoothed tapered tip enters the threaded aperture thus permitting the threaded flexible body to be screwed into the threaded aperture until the fracture is properly and sufficiently compressed and fixed. In this manner it is possible to compress and fix the fracture immediately adjacent the fracture without the need for more than one incision and insures the accuracy of alignment during the fixation process. A cast is often used during the initial healing period. In certain selected cases where fixation is secure in firm bone without fragmentation, the surgeon may decide not to use a cast after implantation of the device.

The invention accordingly, comprises the features of construction, combination of elements, and arrangements of parts which will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings in which:

FIG. 1 shows a top view application of the orthopedic fixation device to the ulna.

FIG. 2 shows a side view application of the orthopedic fixation device to the ulna.

FIG. 3 shows a fracture of the upper end of the ulna.

FIG. 4 shows a top view of prior art orthopedic fixation device to the ulna.

Similar reference characters refer to similar parts throughout the several views of the drawings.

DETAILED DESCRIPTION OF THE PREFERRED EMBODIMENT

As shown in FIGS. 1 and 2, the present invention relates to an orthopedic fixation device and method for fixation of bone fractures generally indicated as 10. As more fully described hereinafter, the orthopedic fixation device 10 comprises a unique three point fixation that more rigidly immobilizes the fracture greatly enhancing the compression at the fractured surfaces to improve healing.

The orthopedic fixation device 10 comprises a first substantially rigid fixation member 12 and second fixation member 14. The fixation member 12 comprises an enclosed head 16 having a groove 18 formed on the outer surface thereof and an elongated body 20 having a threaded aperture 22 formed on the mid-portion thereof and a threaded outer portion 24. The second fixation member 14 comprises an elongated substantially flexible pin comprising a threaded flexible body 26 having a smooth tapered tip 28 at one end thereof and a head 30 having a groove 32 formed on the outer surface thereof at the opposite end thereof. In addition, a washer 34 may be used to prevent the head 30 from cutting through the proximal ulnar bone fragment on the tightening of the elongated pin 14.

The orthopedic fixation device 10 is used in the repair of a fractured ulna as best shown in FIGS. 1 and 2 near the elbow along fracture line 36 using the unique three point fixation and implantation by direct visualization that represents a significant improvement over the prior art, particularly in complex fractures.

FIG. 4 best typifies the most pertinent prior art as disclosed in U.S. Pat. No. 3,763,855. As disclosed, the fixation device generally indicated as 40 comprises a first and second fixation member 42 and 44 respectively. As shown, the first fixation member 42 comprises a body 46 having an asymmetric enlarged head 48 and smooth portion 50 found on opposite ends thereof. A threaded aperture 52 is formed adjacent the outer end of the smooth body 46. The second fixation member 44 comprising an elongated flexible pin 54 having a threaded portion 56 formed on the outer surface thereof. An enlarged head 58 and tapered tip 60 are formed on opposite ends of the elongated body 54. Notwithstanding the apparent similarities with the instant invention are only superficial since the two point fixation device 40 using a plug fit type technique is clearly inferior in application. Specifically the McAtee fixation device 40 is applied or implanted by making two incisions in patient's arm. A first incision is made at the elbow ulnar fracture site in the area of the olecranon process. A hole is then drilled through the olecranon in line with the marrow canal of the ulna. A second incision is made two inches distal to the fracture site to expose the posterior-medial aspect of the ulna. A second hole is drilled through the flat posterior-medial surface and into the marrow canal of the ulna.

The first fixation member 42 is then plugged or fitted through the second incision through the outer portion of the ulna and extends into the marrow canal. Due to the long distance between the two incisions it is necessary to blindly align the tapered tip 60 of the second fixation member 44 down the marrow canal of the ulna to the threaded aperture 52 of the first fixation member 42. In order to accomplish this blind, non-visual alignment, a special tool (not shown) must be used in attempting control both lateral and rotation alignment.

Once aligned the first and second fixation member 42 and 44 may then be secured relative to each other. Unfortunately the location of the threaded aperture 52 adjacent the outer end of the body 46 and the relative position of the outer end within the marrow canal permits the first fixation member 42 to move once implanted. This inherent instability of only two points of fixation (one at proximal ulna by head 58 and the other at the one surface of the ulna at the distally placed device 42) limits the amount of compression that may be applied between the fractured surface and may even permit the first fixation member 42 to move or work loose in the ulna.

In constrast the present orthopedic fixation device and method provides a rigid three point mechanical fixation employing a relatively simple application. Specifically, the fracture site is typically approached by making a single incision at the proximal end of the ulna. This is a posterior type of surgical approach with the incision centering over the proximal ulnar fracture. It begins at the distal arm above the elbow and extending to the proximal ulnar area. The hollow marrow cavity of the distal ulna is cleared of the soft tissue in the region of the fracture with a bone currette. The bone currette is used to probe the marrow cavity to determine its axial alignment. The fracture site is inspected and cleared of blood clot and debris. A first channel A is then drilled through the olecranon 64 in alignment with the marrow canal 66 of the ulna. A second channel B is drilled laterally through the surface of the outer portion 68 of the ulna through the marrow canal 66 and into the opposite cortex or inner portion 70. Since the first fixation member 12 includes a threaded outer portion 24, the first fixation member 12 may be securely attached immediately adjacent the fracture. This permits a single incision method, and implantation by direct visual alignment. The threaded flexible body 26 is then passed through the first drilled hole A such that the smoothed tapered tip 28 enters the threaded aperture 22 thus permitting the threaded flexible body 26 to be screwed into the threaded aperture 22 until the fracture is properly and sufficiently compressed and fixed. The resultant three point fixation indicated as C, D and E, immobilized the fracture permitting a high degree of compression enhancing healing between the fracture surface. This is due in large part since the first fixation member 12 is fixed to opposite sides of the ulna such that the fixation member 12 and 14 remain perpendicular relative to each other during and after implantation. Moreover, it is possible to compress and immobilize the fractured surfaces relative to each other immediately adjacent the fracture with a single incision and insures the accuracy of alignment during the fixation process. The three points of fixation are both corteses of the ulnar at points C and D of the first fixation member 12 and at point E of the olecranon process of the proximal ulnar fragment at the second fixation member 14.

This orthopedic device 10 is specifically adapted for use with the ulnar bone of the forearm at the elbow. However, it is evident that the application of this principle can be applied in many other fracture sites in the body and for treatment of such fractures.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative.

It is also to be understood that the following claims are intended to cover all of the generic and specific features of the invention which, as a matter of language, might be said to fall therebetween.

Now that the invention has been described,
What is claimed is:

1. An orthopedic fixation device primarily designed to accomplish a three point fixation of a bone fragment relative to a main part of a fractured bone and comprising in combination: a first fixation member being substantially rigid and including an internally threaded aperture formed therein intermediate its opposite ends, and having a head at a proximal end thereof, said first fixation member further including an externally threaded surface portion formed on an exterior surface of said first fixation member between said internally threaded aperture and the distal end of said first fixation member, said externally threaded surface portion being adapted to be disposed to securely engage a predetermined portion of the main part of the fractured bone, whereby said first fixation member is adapted to be mounted on the interior of the main part of the fractured bone; a second fixation member comprising an elongated, substantially flexible pin having an externally threaded surface portion extending along a predetermined portion of the length thereof, said pin having a transverse dimension along said externally threaded surface portion sufficient to accomplish threaded attachment within said aperture of said first fixation member when disposed in aligned engaging relation therewith, said second fixation member adapted to be disposed on the interior of both the bone fragment and the main part of the fractured bone and to extend along the longitudinal dimension of the main part of the fractured bone on the interior thereof and into anchoring engagement with said first fixation member, whereby inspection and fixation of the bone fragment and the main part of the fractured bone is accomplished.

2. An orthopedic fixation device as in claim 1 wherein said first fixation member is dimensioned to be mounted at least in part on the interior of the main part of the fractured bone and in substantially transverse relation to the longitudinal axis thereof, said externally threaded surface portion to be disposed in anchored engagement with a predetermined portion of the main part of the fractured bone located opposite to a portion of the main part of the fractured bone for engaging said head of the first fixation member.

3. A method of accomplishing fixation and compression between a bone fragment and a main part of the fractured bone comprising the steps of:
 (a) making a first incision at the site of fracture between the bone fragment and the main part of the fractured bone and cleaning the site of debris and blood clot,
 (b) cleaning the marrow cavity of the main part of the ulna of soft tissue,
 (c) aligning the bone fragment and the main part of the fractured bone,
 (d) drilling a first hole into the main part of the fractured bone transverse to the length thereof and through the marrow canal and the cortex on opposite sides of the marrow canal,
 (e) dispensing a first fixation member into said first hole and anchoring the distal end thereof into the correspondingly positioned cortex through a threaded connection therebetween,
 (f) the proximal end of the fractured bone is drilled and through the bone fragment starting at the proximal aspect of the olecranon extending to the main part of the fractured bone so as to extend longitudinally into and along the marrow canal,
 (g) interconnecting a second fixation element having a head thereon with said first fixation element through threaded engagement between the outer surface of the second fixation element and a interiorly threaded aperture formed in said first fixation element intermediate the ends thereof, and
 (h) adjusting the threaded engagement between said second and first fixation elements until the desired force is exerted on the bone fragment and the main part of the fractured bone.

4. A method as in claim 3 further comprising the steps of drilling said first hole in the main part of the fractured bone in spaced apart, close proximity to the fracture site between the bone fragment and the main part of the fractured bone.

5. A method as in claim 3 comprising drilling the first hole in a portion of the main part of the fractured bone exposed by the provision of the incision in close proximity to the fracture site.

* * * * *